US006892734B1

(12) United States Patent
Schleicher et al.

(10) Patent No.: US 6,892,734 B1
(45) Date of Patent: May 17, 2005

(54) WOUND CARE SUSPENSION SYSTEM

(76) Inventors: Thomas R. Schleicher, 5650 N. Sheridan, 17H, Chicago, IL (US) 60660; R. Gary Diaz, 53 Martins La., Highland Park, IL (US) 60035; John W. Callahan, 11434 Bittersweet Creek Run, Fort Wayne, IL (US) 46814

( * ) Notice: Subject to any disclaimer, the term of this patent is extended or adjusted under 35 U.S.C. 154(b) by 0 days.

(21) Appl. No.: 09/692,000

(22) Filed: Oct. 19, 2000

(51) Int. Cl.$^7$ .................................................. A61F 13/00
(52) U.S. Cl. ........................... 128/889; 602/41; 602/61; 5/654
(58) Field of Search ................................ 602/5, 41, 42, 602/43, 47, 58, 59, 60, 75, 61, 62; 128/877, 888, 889, 892, 894, 891, 893; 5/652.1, 654, 490, 710, 713, 715

(56) References Cited

U.S. PATENT DOCUMENTS

| 3,468,311 A | * | 9/1969 | Gallagher .................... 604/370 |
| 4,500,316 A | | 2/1985 | Damico ....................... 604/389 |
| 4,550,439 A | | 10/1985 | Peppiatt et al. ................. 383/8 |
| 4,614,000 A | * | 9/1986 | Mayer ........................... 5/484 |
| 4,704,116 A | | 11/1987 | Enloe .......................... 604/385 |
| 4,962,769 A | * | 10/1990 | Garcia ......................... 128/889 |
| 5,105,490 A | * | 4/1992 | Shek ............................ 5/693 |
| 5,147,343 A | | 9/1992 | Kellenberger ............... 604/368 |
| 5,288,546 A | | 2/1994 | Roessler et al. ............. 428/284 |
| 5,310,402 A | * | 5/1994 | Rollband ...................... 602/42 |
| 5,364,339 A | * | 11/1994 | Carver .......................... 602/47 |
| 5,394,577 A | * | 3/1995 | James et al. .................... 5/713 |
| 5,413,570 A | | 5/1995 | Enloe ........................ 604/385.2 |
| 5,415,644 A | | 5/1995 | Enloe ........................ 604/385.2 |
| 5,599,290 A | * | 2/1997 | Hayes et al. ................... 602/61 |
| 5,599,338 A | | 2/1997 | Enloe ........................ 604/385.2 |
| 5,720,714 A | * | 2/1998 | Penrose ........................ 128/888 |
| 6,018,092 A | * | 1/2000 | Dunshee ........................ 602/59 |
| 6,519,797 B1 | * | 2/2003 | Brubaker et al. .............. 5/654 |
| 6,591,437 B1 | * | 7/2003 | Phillips .......................... 5/710 |

* cited by examiner

Primary Examiner—Nicholas D. Lucchesi
Assistant Examiner—Quang D Thanh
(74) Attorney, Agent, or Firm—Michael R. McKenna

(57) ABSTRACT

A suspension system for the care and prevention of wounds on the body of a user includes an array of removable suspension devices forming a flexible sheet. Each suspension device is removably coupled to at least one other suspension device. The suspension devices are selectably removable from the array in order to define a space within the sheet which approximates the size of a target area on the body of the user. A disposable garment for the body of a user includes an absorbent portion and a wound care and prevention suspension portion. The absorbent portion has a fluid pervious inner sheet, a fluid impervious outer sheet and at least one layer of absorbent material disposed between the inner and outer sheets. The wound care and prevention suspension portion is coupled to the absorbent portion. The application of a suspension system for the care and prevention of wounds to the body of a user including identifying a target area on the body of the user, obtaining a sheet formed of removable suspension devices, selectably removing at least one suspension device from the sheet to define a space which approximates the target area, and securing the sheet to the body of the user such that the sheet supports the target area without contacting the target area.

22 Claims, 9 Drawing Sheets

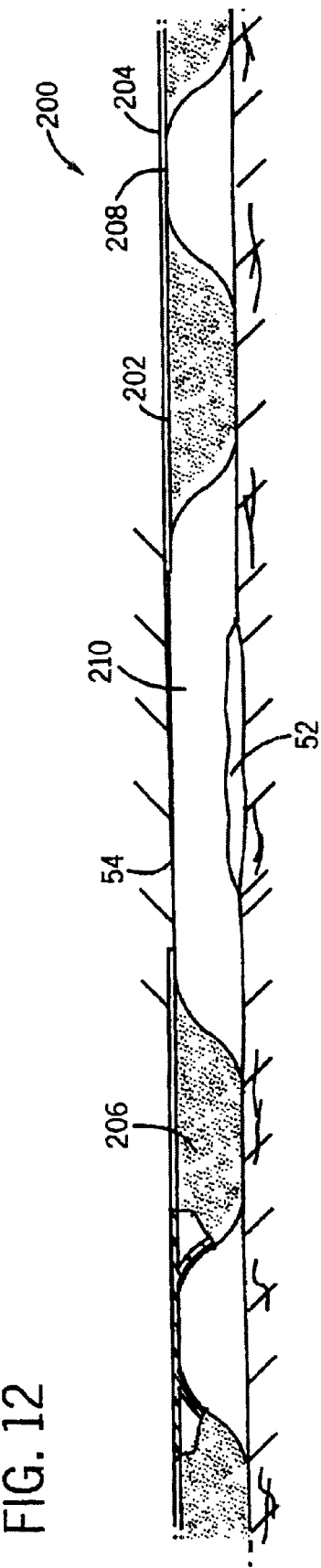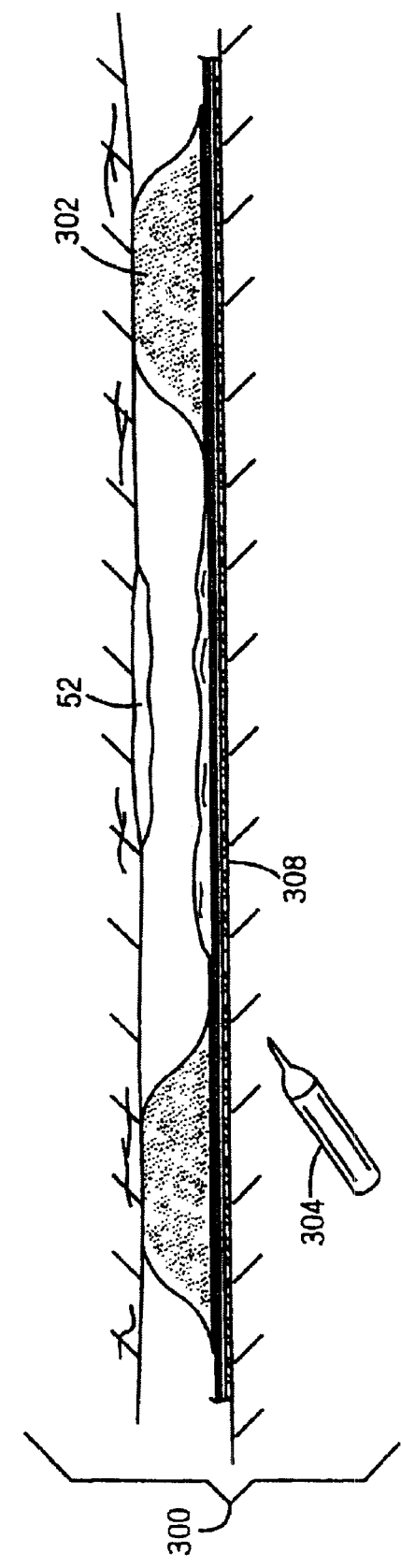

WOUND CARE SUSPENSION SYSTEM

FIELD OF THE INVENTION

The present invention relates to the field of wound care systems.

BACKGROUND OF THE INVENTION

Persons with existing wounds resulting from, for example, medical procedures, burns, traumatic injuries, or decubitus ulcers, often have difficulty resting on surfaces such as a bed, due to the pain and irritation associated with contact between the wound and the resting surface. Additionally, persons who are confined to a bed for an extended period of time, typically lie in a supine position, and may develop decubitus ulcers, particularly on the buttocks or the lower back. The four main causes of decubitus ulcers, individually or in any combination, are pressure, friction, shear and moisture resulting from prolonged contact between the person's body and the bed or the bed sheets. The treatment of decubitus ulcers of the buttocks or the lower back is further complicated for those bedridden patients who also experience incontinence. Bodily excretions, including urine and feces, can irritate existing decubitus ulcers or areas of the patient's body susceptible to decubitus ulcers.

Support devices for the care of wounds such as pads, pillows, and cushions are known. These devices typically include at least one layer of material to support and cushion a wound. Such devices are typically loosely positioned under, or adjacent to, the user. In some instances, multiple support devices can be positioned adjacent to the user to create a gap which is approximately positioned at the location of user's wound. Adjustable mattresses, for the prevention of decubitus ulcers, are also known. Such mattresses vary the load placed on a person's skin by adding or removing air, in a programmed manner, to and from specific areas of the mattress.

Existing support devices and adjustable mattresses have a number of drawbacks. Existing support devices typically provide uneven support to person's body, particularly at the area of the wound and the area immediately surrounding the wound. Existing support devices are typically loosely positioned next to the body of the user and are often easily dislodged and mispositioned. Such devices typically require continual readjustment in response to movement and repositioning of the user. Additionally, existing support devices typically do not eliminate frictional or direct contact of the device with the wound. Existing adjustable mattresses and the typical support devices do not locally suspend the wound or potential wound area and are not configurable to specific wound sizes and shapes. Further, existing support devices and adjustable mattresses do not typically accommodate bodily excretions. Moreover, existing adjustable mattresses are expensive, not disposable, and often difficult to maintain and operate.

Accordingly, it would be advantageous to provide a system for the care and prevention of wounds that overcomes these and other disadvantages of existing support devices and adjustable mattresses. A significant need exists for a system for the care and prevention of wounds which enables a person to rest on a generally horizontal surface, such as a bed, without irritating an existing wound or an area susceptible to decubitus ulcers. A need exists for a system to evenly and comfortably suspend the locations of decubitus ulcers, or the locations most susceptible to development of decubitus ulcers, above a resting surface. A need also exists for a system which eliminates the four main causes of decubitus ulcers, pressure, friction, shear and moisture. What is needed is a wound care suspension system which is easily custom fit to support specific wounds of different sizes or shapes. What is also needed is a wound care suspension system that is inexpensive, easy to apply to a patient and disposable. It would be advantageous to develop a wound care suspension system which is configured to accommodate bodily excretions in order to minimize the effect of such excretions on wounds or potential wound locations.

SUMMARY OF THE INVENTION

The present invention provides a system for the care and prevention of wounds which enables a person to rest on a generally horizontal surface without irritating an existing wound or an area susceptible to wounds by eliminating direct or frictional contact with the area. The present invention evenly and comfortably suspends locations of, or locations susceptible to, decubitus ulcers or other wounds above a resting surface. The present invention is easily custom fit to support specific wounds. Additionally, the present invention is inexpensive, easy to apply and disposable. The present invention can also be configured to accommodate bodily excretions.

The present invention provides a device system for the care and prevention of wounds on the body of a user. The device includes an array of removable cells forming a flexible sheet. Each cell is removably coupled to at least one other cell. The cells are selectably removable from the array in order to define a space within the sheet which approximates the size of a target area on the body of the user.

According to another aspect of the invention, a disposable garment for the body of a user includes an absorbent portion and a wound care and prevention portion. The absorbent portion has a fluid pervious inner sheet, a fluid impervious outer sheet and at least one layer of absorbent material positioned between the inner and outer sheets. The wound care and prevention portion is coupled to the absorbent portion. The suspension portion includes an array of removable suspension devices forming a generally flexible suspension sheet. The suspension devices are selectably removable from the array in order to define a space within the sheet which approximates the size of a target area on the body of the user.

According to another aspect of the invention, a disposable garment for the body of a user includes an absorbent portion and a wound care and prevention portion. The wound care and prevention suspension portion is coupled to the absorbent portion. The suspension portion includes an array of removable gas-filled bubbles forming a generally flexible suspension sheet. The bubbles are selectably deflatable from the array in order to define a recess within the sheet which approximates the size of a target area on the body of the user.

The present invention also provides for the application of a suspension system for the care and prevention of wounds to the body of a user including identifying a target area on the body of the user, and obtaining a sheet formed of removable suspension devices. Application of the present invention further provides selectably removing at least one suspension device from the sheet to define a space which approximates the target area, and securing the sheet to the body of the user such that the sheet supports the target area without contacting the target area.

Various advantages and features of the invention will be readily apparent from the following description of the preferred embodiments taken in conjunction with the accompanying drawings described below.

BRIEF DESCRIPTION OF THE DRAWINGS

FIG. 12 is a sectional view of a wound care suspension system in accordance with another alternative preferred embodiment of the present invention; and FIG. 13 is a sectional view of a wound care and suspension system in accordance with another alternative preferred embodiment of the present invention.

DETAILED DESCRIPTION OF THE PREFERRED EMBODIMENTS

Figure 1:
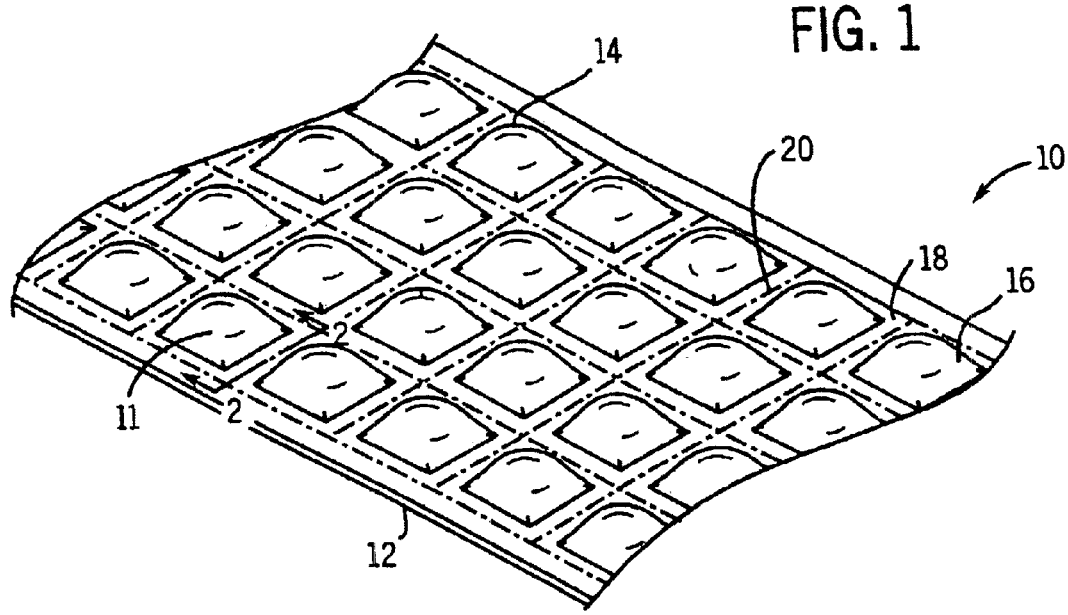
FIG. 1 is a top perspective view of a wound care suspension system in accordance with a preferred embodiment of the present invention.

Referring to FIG. 1, a portion of a wound care system 10 for the care and prevention of wounds is shown. The system 10 includes an array 11 of removable suspension devices coupled to a backing 12 to form a flexible sheet 14. In a preferred embodiment, the suspension devices are a sheet of fluid filled bubbles 16. Each fluid filled bubble 16 can be generally square and extend upwardly from an inner surface of the backing 12. The bubbles 16 are preferably aligned in a matrix to form the array 11. Alternatively, the bubbles 16 can be arranged in a non-uniform manner along the backing 12. The bubbles 16 are preferably arranged such that each bubble is connected to at least one side of at least one other bubble 16. The borders between the bubbles 16 include perforations 20. The perforations 20 facilitate the removal of one bubble 16 from the array 11 and enable air to pass through the border of the bubbles 16 to ventilate the portion of the user's body in contact with the suspension system 10. The suspension system 10 is configured to conform to, and comfortably and evenly suspend, the portion of the user's body placed in contact with the suspension system 10.

Figure 2:
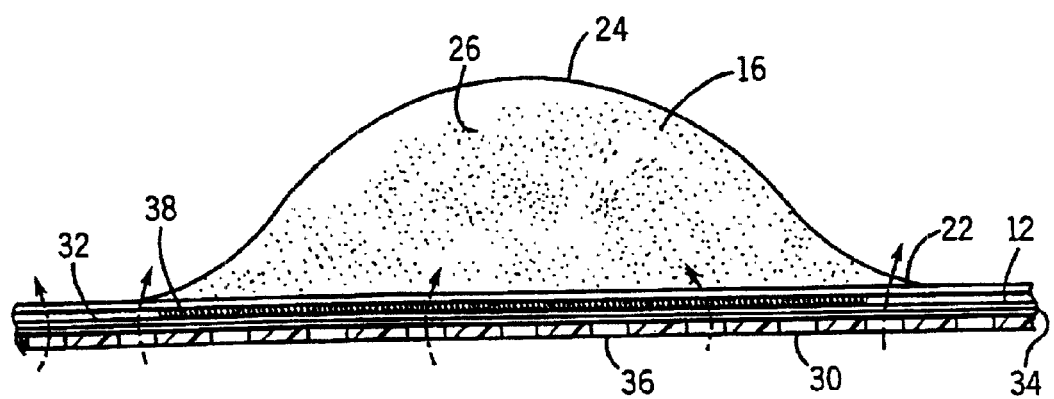
FIG. 2 is a sectional view of the wound care suspension system taken substantially along line 2—2 of FIG. 1.
Figure 3:
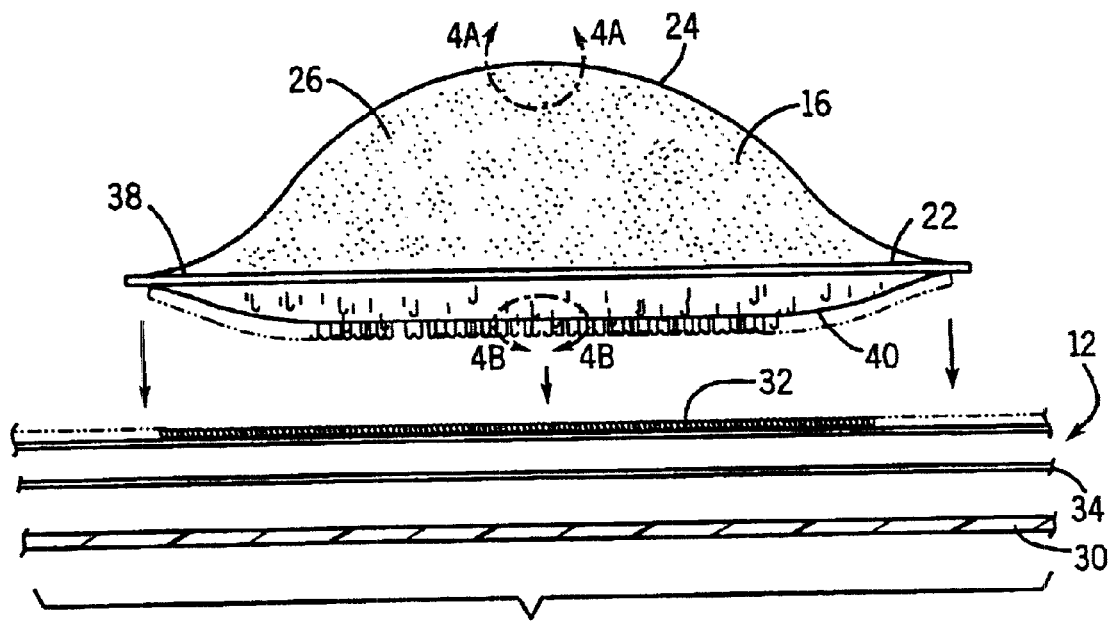
FIG. 3 is an exploded sectional view of a backing and a removable bubble of the wound care suspension system of FIG. 1.

FIGS. 2 and 3 illustrate one of the bubbles 16 and the backing 12 in greater detail. Each bubble 16 is an inflated element having a generally flat, square base layer 22 and a generally convex user contact layer 24. The base layer 22 and the contact layer 24 define an inner cavity 26 of the bubble 16 which is filled with a fluid, preferably air. Alternatively, the bubbles 16 can be filled with other fluids such as, for example, oxygen, nitrogen, another conventional gas, water, or a conventional gel material. Each bubble 16 is removably connected to the backing 12. In a preferred embodiment, each bubble 16 is removably connected to the backing 12 through a hook and loop type fastener. Alternatively, the bubbles 16 can be removably attached to the backing 12 through other fastening means such as, for example, adhesives, snap fits, buttons, and zippers. The bubbles 16 are configured to comfortably suspend a portion of the user's body in contact with the suspension system 10 above a resting surface. In a preferred embodiment, each bubble 16 is approximately one square inch in size and is configured to sustain or to retain the fluid at an applied pressure of at least 25 psi. The bubble 16 is preferably removably connected to the backing 12 in a manner which requires a force of approximately eight pounds in order to remove the bubble 16 from the backing 12. In alternative embodiments, the bubbles 16 can have other shapes such as, for example, circular, oval, polygonal, irregular, or a combination thereof.

The backing 12 is a flexible sheet which is configured to removably connect to the bubbles 16. The backing 12 includes an outer base layer 30 and a bubble contact layer 32. The outer base layer 30 is connected to the bubble contact layer 32 of the backing 12 by a layer of adhesive 34, such as a glue. In another preferred embodiment, the outer base layer 30 is heat bonded to the bubble contact layer 32. The outer base layer 30 has a plurality of perforations 36 which preferably generally align with the perforations 20 within the array of bubbles 16. The perforations 36 enable air to pass through the outer base layer 30 for ventilation and enable a user to easily and selectably remove a portion of the backing 12. The outer base layer 30 of the backing 12 is preferably made of a heat sealable plastic and, alternatively, can be made of other materials such as, for example, other plastics, cloth or silk. The backing 12 provides a flexible, breathable, lightweight and durable support sheet for the suspension system 10. In a preferred embodiment, the bubble contact layer 32 of the backing 12 is a woven sheet which includes a plurality of outwardly extending loops configured to easily and removably connect to the bubbles 16. Alternatively, the bubble contact layer 32 of the backing 12 can be made of other materials, such as, for example, unwoven cloth or plastic. In an alternative embodiment, the bubble contact layer 32 can be made of a "hook" material.

Figure 4A:
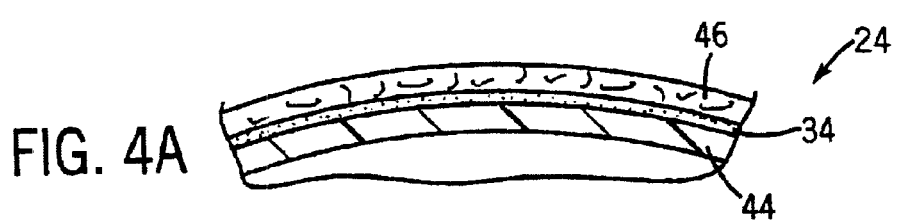
FIG. 4A is a sectional view of a contact layer of the bubble taken substantially along line 4A—4A of FIG. 3.
Figure 4B:
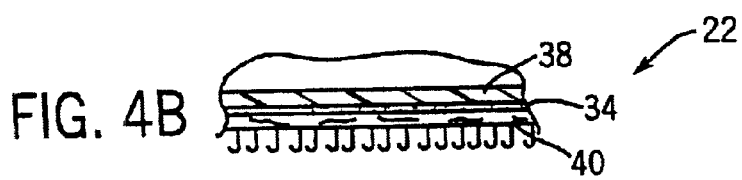
FIG. 4B is a sectional view of a backing contact layer of the bubble of the wound care suspension system taken substantially along line 4B—4B of FIG. 3.

As best shown in FIGS. 3 and 4B, the base layer 22 of each bubble 16 includes a main sheet 38 affixed to a backing contact layer 40 by the adhesive 34. The layer 22 is configured to easily and removably connect to the backing 12. In a preferred embodiment, the main sheet 38 is heat bonded to the backing contact layer 40. The main sheet 38 is preferably made of a heat sealable plastic and, alternatively, can be made of other materials such as, for example, other plastics, cloth or silk. The main sheet 38 is configured to retain the fluid within the bubble 16 at the required pressure. In a preferred embodiment, the backing contact layer 40 of the bubble 16 is a woven sheet which includes a plurality of outwardly extending hooks configured to easily and removably connect to the backing 12. In a particularly preferred embodiment, the hooks are "micro-J" hooks. Alternatively, the backing contact layer 40 of the bubble 16 can be made of other materials, such as, for example, unwoven cloth or plastic. In an alternative embodiment, the backing contact layer 40 can include loop material.

As best shown in FIGS. 3 and 4A, the user contact layer 24 of each bubble 16 includes an inner support layer 44 affixed to a cushionable layer 46 by the adhesive 34. In another preferred embodiment, the inner support layer 44 is heat bonded to the cushionable layer 46. The inner support layer 44 is preferably made of a heat sealable plastic and, alternatively, can be made of other materials such as, for example, other plastics, cloth or silk. The inner support layer 44 is formed to a portion of the main sheet 38 of the base layer 22 and is configured to retain the fluid within the bubble 16 at the required pressure. The cushionable layer 46 is made of a soft material such as, for example, cotton or silk. The cushionable layer 46 provides a soft, comfortable layer of material for contact with the user's body.

Figure 5A:
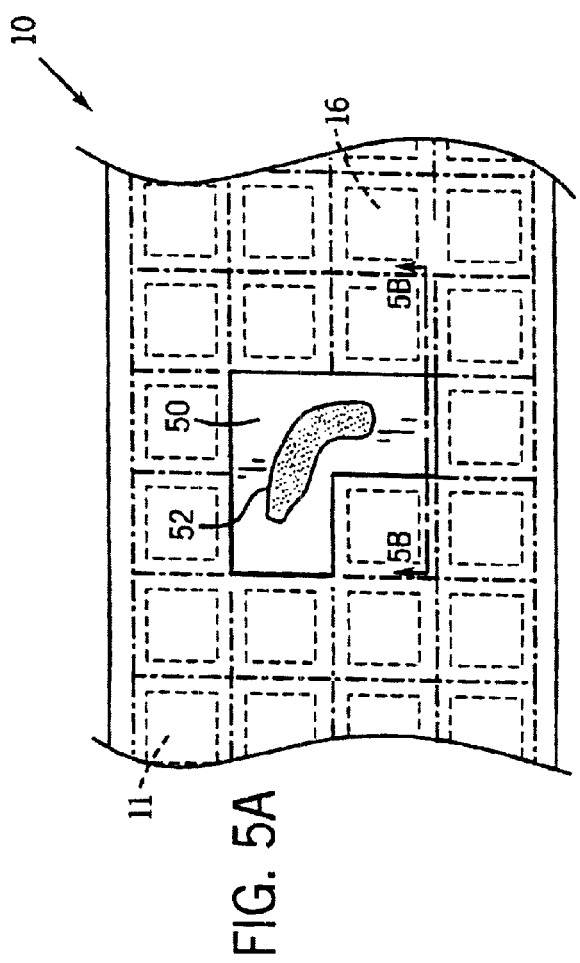
FIG. 5A is a top view of a portion of the wound care suspension system of FIG. 1 with three of the bubbles removed from the suspension system.

FIG. 5A shows the suspension system 10 in greater detail. The suspension system 10 includes the array 11 of bubbles 16. The array 11 of bubbles 16 are configured for selective removal by the user, or other person, from the array 11, individually or in groups, in order to define a custom fit opening 50 within the suspension system 10. The custom fit opening 50 is sized to specifically match a target area 52 on the user's body. The target area 52 can be the site of a decubitus ulcer, or other wound such as a burn, a traumatic injury wound, or a medical procedure wound. The target area 52 can also be an area susceptible to decubitus ulcers or other wounds. The selective removal of bubbles 16, individually or in groups, from the array 11 of bubbles 16 enables any user to easily and quickly size the opening 50 to the specific needs of the particular user.

Figure 5B:
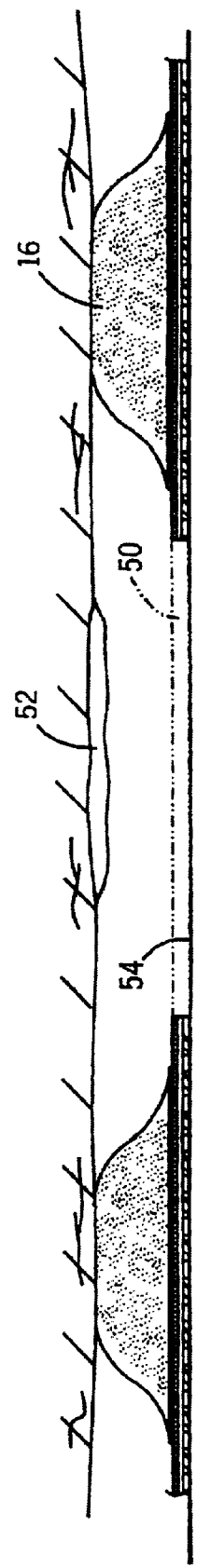
FIG. 5B is a sectional view of the wound care and suspensions of FIG. 1 system taken substantially along line 5B—5B of FIG. 5A.

As best illustrated in FIG. 5B, the removal of select bubbles 16 from the suspension device 10 preferably includes the removal of the corresponding portion(s) of the backing 12 adjacent to the removed bubbles 16. The removal of the selected bubbles 16 enables the remaining bubbles 16 within the suspension device 10 to comfortably and evenly support the portion of the user's body in contact with the suspension device 10 and to comfortably suspend the target area 52 of the user's body above and away from a resting surface 54, such as a bed surface or bed sheets. The suspension device 10 comfortably and evenly suspends the target area 52 of the user above the resting surface 54, and eliminates direct and incidental frictional contact of the target area 52 with the resting surface 54. The suspension device 10 also eliminates the shear and stress associated with contact of the target area 52 with a resting surface 54, thereby enabling the wound to heal while the user comfortable rests in a supine position or other resting position. Moreover, the gap created at the opening 50 between the target 52 and the resting surface 54 along with the perforations 20, 36 inhibit the accumulation of moisture at the target area 52.

Figure 6A:
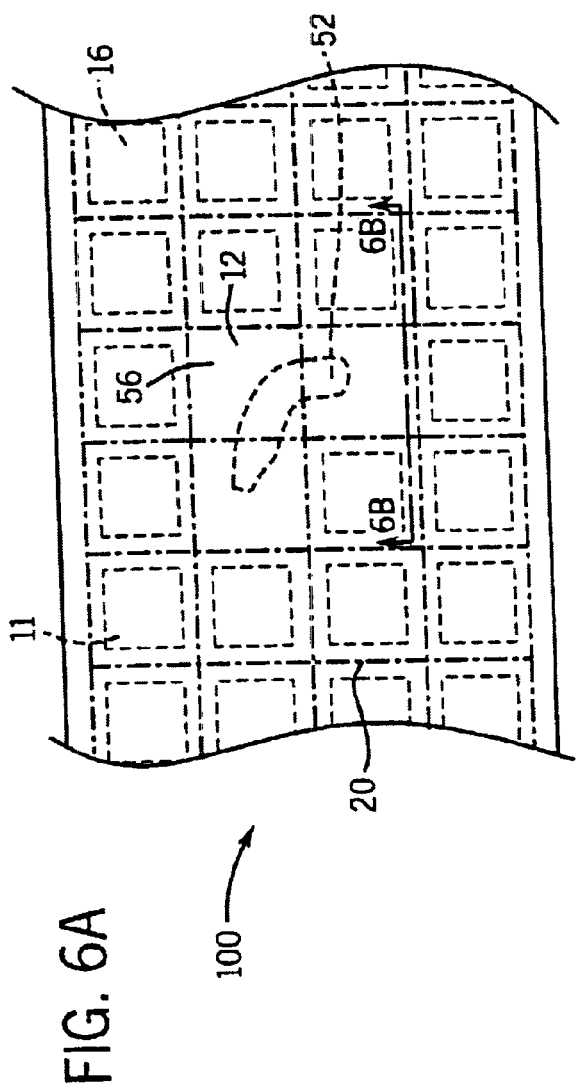
FIG. 6A is a top view of a portion of a wound care suspension system in accordance with an alternative embodiment of the present invention.
Figure 6B:
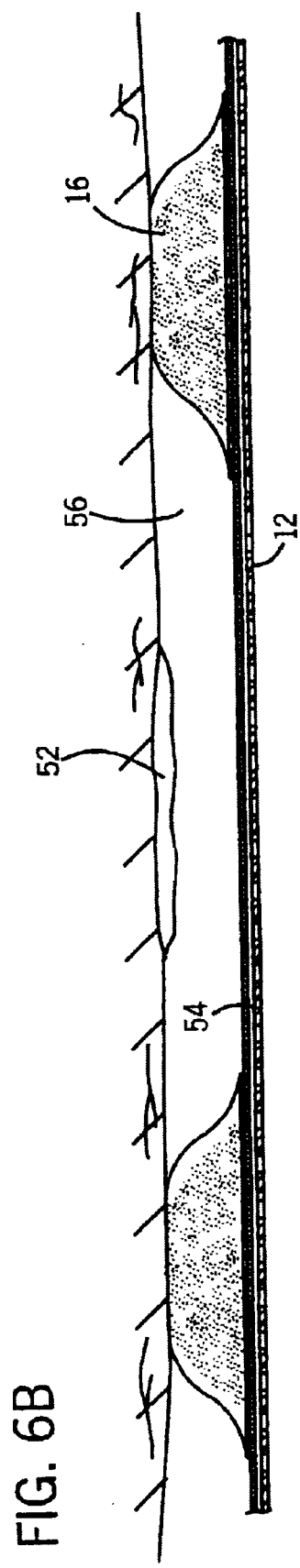
FIG. 6B is a sectional view of the wound care and suspension system taken substantially along line 6B—6B of FIG. 6A.

In an alternative preferred embodiment, as shown in FIGS. 6A and 6B, the bubbles 16 of the suspension system 10 are selectably removed from the backing 12, individually or in groups, thereby creating a space 56 (or a recess) between the backing 12 and the target area 52 of the user's body. The remaining bubbles 16 within the array 11 thereby continue to comfortably and evenly support the portion of the user's body above the resting surface 54 and also comfortably and evenly suspend the target area 52 of the user's body away from the backing 12 of the suspension device 10. The configuration of the suspension system 10 of FIGS. 6A and 6B enables the outer surface of the suspension system 10 to remain covered thereby preventing exposure of the target area to the outer environment. The perforations 20 and 36 within the backing 12 and the borders of the bubbles 16 enable air to flow through the suspension system 10 and into the space 56 between the backing 12 and the target area 52. This embodiment may be preferred for ambulatory patients, who can rely on the backing 12 of the suspension device 10 in order to substantially shield the target area 52 from view when the user is wearing the suspension system 10 in a non-supine position.

The suspension system 10 is suitable for use on any portion of a user's body with a wound or any portion susceptible to a wound. The suspension system 10 can be produced in a number of different shapes and sizes to match particular needs of users of all sizes. The suspension system 10 may be positioned adjacent to the user's body, one or more of the bubbles 16 can removed to custom define a space over the wound area and the suspension system 10 can be connected to the user through tape, straps or other conventional means. The suspension system 10 may also be incorporated into a disposable garment.

Figure 7:
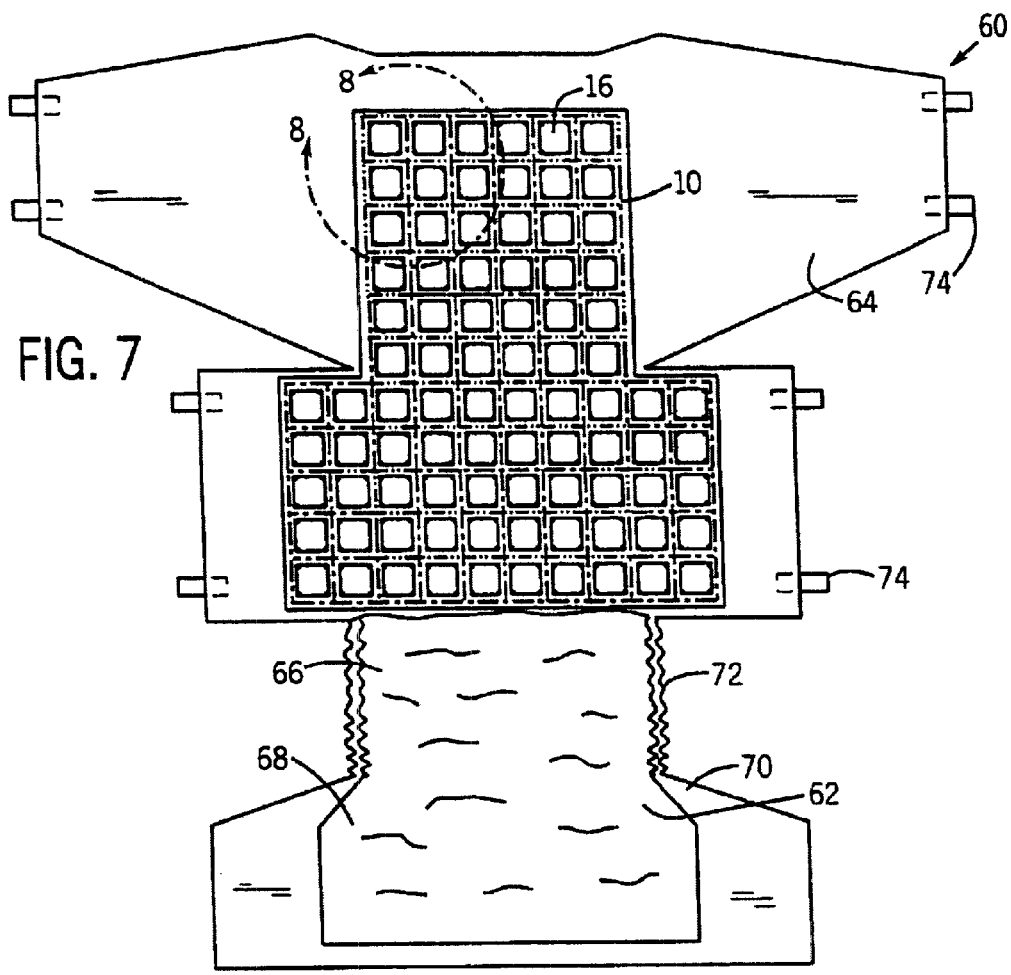
FIG. 7 is a top perspective view of a disposable garment with a wound care suspension system in accordance with a preferred embodiment of the present invention.

FIG. 7 illustrates a disposable garment 60 which includes the suspension system 10 for the care and prevention of wounds. In a preferred embodiment, the disposable garment 60 is a diaper including the suspension system 10, an absorbent portion 62 and a plurality of panels 64. The absorbent portion 62 is a flexible member including a fluid pervious inner sheet 66, at least one layer of absorbent material 68 and a fluid impervious outer sheet 70. The absorbent portion 62 is connected to the suspension system 10. In a preferred embodiment, the absorbent portion 62 is stitched to the suspension system 10. The absorbent portion 62 functions to absorb bodily excretions, such as urine and feces, and to retain the excretions within the at least one layer of absorbent material 68 of the absorbent portion 62. The absorbent portion 62 also assists in preventing the excretions from passing through the impervious outer sheet 70 and from extending into the suspension system 10 of the disposable garment 60. The disposable garment 60 facilitates the positioning of the suspension system 10 against the user's body and secures the suspension system 10 to the user's body during use. In a preferred embodiment, the suspension system 10 is connected to one of the fluid impervious inner sheet 66 and the fluid impervious outer sheet 70. In another preferred embodiment, the fluid impervious outer sheet 70 is integrally formed with the backing 12 of the suspension system 10. The garment 60 can be produced in different sizes to accommodate users of all sizes and also to enable varying sections of the user's body, such as, the buttocks, the lower back area or the middle back area, to be comfortably and evenly supported by the suspension system 10.

The fluid pervious inner sheet 66 is disposed on the inner surface of the absorbent portion 62 of the disposable garment 60 and is connected at its edges to the fluid impervious outer sheet 70. The fluid pervious inner sheet 66 is made of a fluid pervious material and is configured to allow fluids to pass through the inner sheet 66 and to maintain the inner surface of the fluid pervious inner sheet 66 substantially dry. The absorbent material 68 is formed in at least one layer. The absorbent material 68 is positioned between, and is attached to, either the fluid pervious inner sheet 66 or the fluid impervious outer sheet 70. The absorbent material 68 functions to absorb and retain bodily excretions. The absorbent material 68 may be formed of a wood pulp fluff, cellulose tissue, open cell foam elements, or other conventional absorbent materials. The fluid impervious outer sheet 70 is connected to the fluid pervious inner sheet 66 and is positioned on the outer surface of the absorbent material 68. The fluid impervious outer sheet 70 prevents fluids from passing through the outer sheet 70. The fluid impervious outer sheet 70 is preferably made of plastic and alternatively can be formed of other materials, such as, for example, rubber, or a non-woven material.

In a preferred embodiment, the absorbent portion 62 of the disposable garment 60 portion further includes elastic leg bands 72 attached to opposing sides of the absorbent portion 62 of the disposable garment 60. The leg bands 72 are configured to securely and comfortable fit substantially around the legs of the user to further inhibit the leakage of bodily excretions from the absorbent portion 62 of the disposable garment 60.

The panels 64 extend from the sides of the suspension system 10 and the forward region of the absorbent portion 62 of the disposable garment 60. The panels 64 are configured to comfortably wrap substantially around the waist and abdomen of the user and to releasably couple to another panel 64 through straps 74. In a preferred embodiment, the panels 64 are made of a soft, elastic material. In a preferred embodiment, portions of the panels include loop material and the straps 74 include hook material. Alternate fastening means can also be used for releasably connecting the panels 64 to one another such as, for example, tape, safety pins or quick connect buckles.

Figure 8:
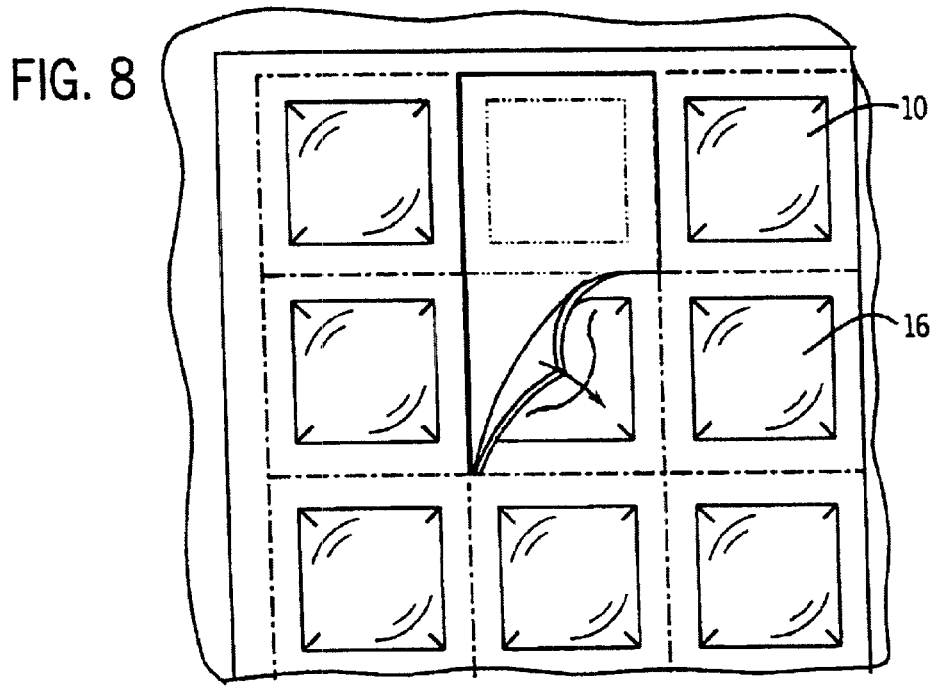
FIG. 8 is a sectional view of a portion of the wound care suspension system taken substantially along line 8—8 of FIG. 7 in which one of the bubbles is shown being removed from the suspension system.

FIG. 8 illustrates the selected removal of an individual bubble 16 from the suspension system 10 of the disposable garment 60. The suspension system 10 is configured to enable the caregiver to easily and selectably remove one or more of the bubbles 16 from the suspension system 10 in order to custom fit the opening 50 in the suspension system 10 to match the target area on the user's body. In a preferred embodiment, the user also removes the portion of the backing 12 corresponding to the selected bubble 16. In an alternative preferred embodiment, shown in FIG. 6B, one or more bubbles 16 are selectably removed from the backing 12 of the suspension system 10 in order to define the space 56 between the target area 52 and the backing 12. The remaining bubbles 16 within the suspension system 10 suspend the target area 52 of the user's body above the resting surface 54.

Figure 9A:
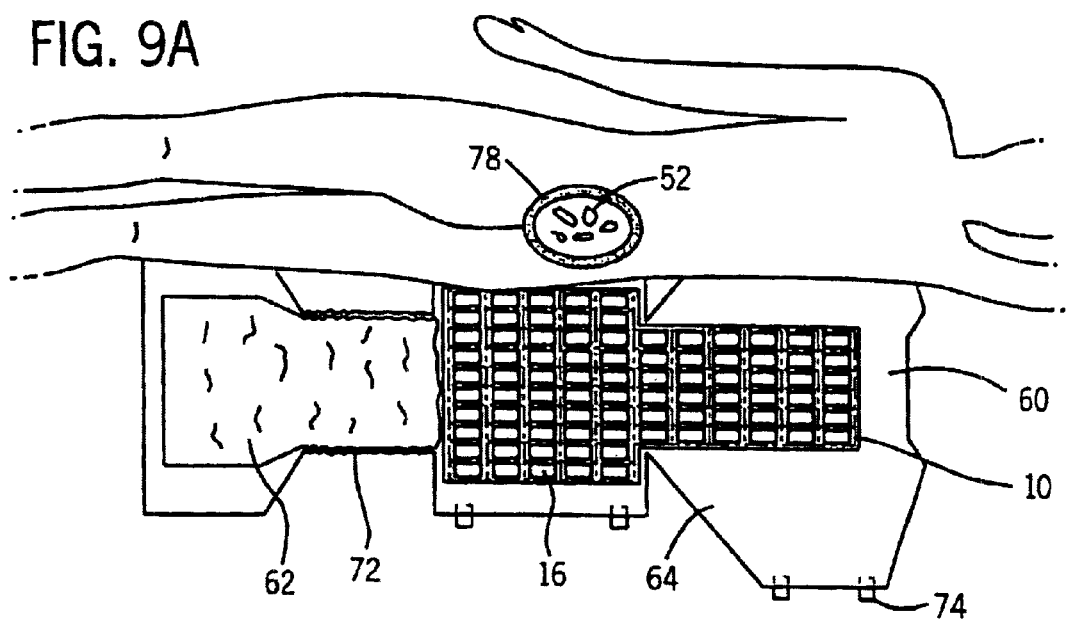
FIGS. 9A through 9F are top perspective views of the application of the disposable garment of FIG. 7 to a user.
Figure 9B:
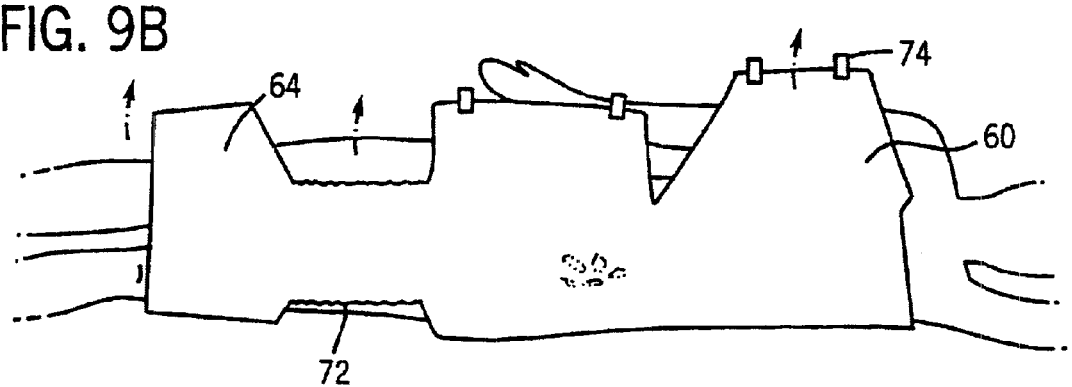

FIGS. 9A through 9F illustrate a method for applying the disposable garment 60 having the suspension system 10 to a user's body. The method includes the steps of identifying the target area 52 on the body of the user. This can be accomplished for example by rolling the user onto his or her side and then applying a dye 78 to the user to mark an outline of the wound or the target area 52, as shown in FIG. 9A. The dye is non-toxic, easily removable dye can be used. In a preferred embodiment, the dye 78 is betadine. The disposable garment 60 is then placed adjacent to the patient. As shown in FIG. 9B, the disposable garment 60 is then positioned up against the patient in the desired position for the suspension system 10.

Figure 9C:
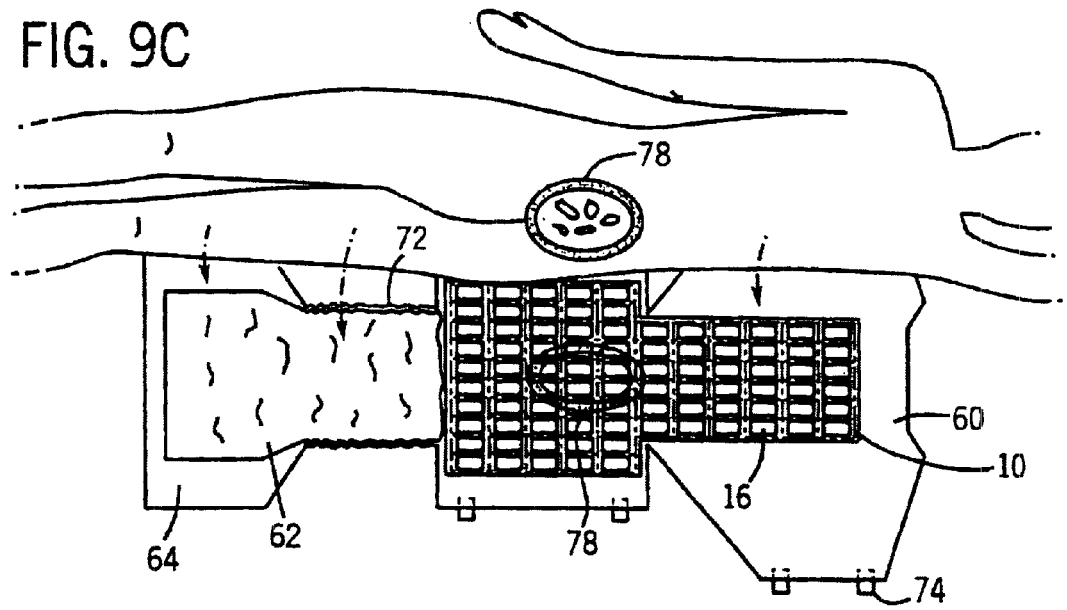
Figure 9D:
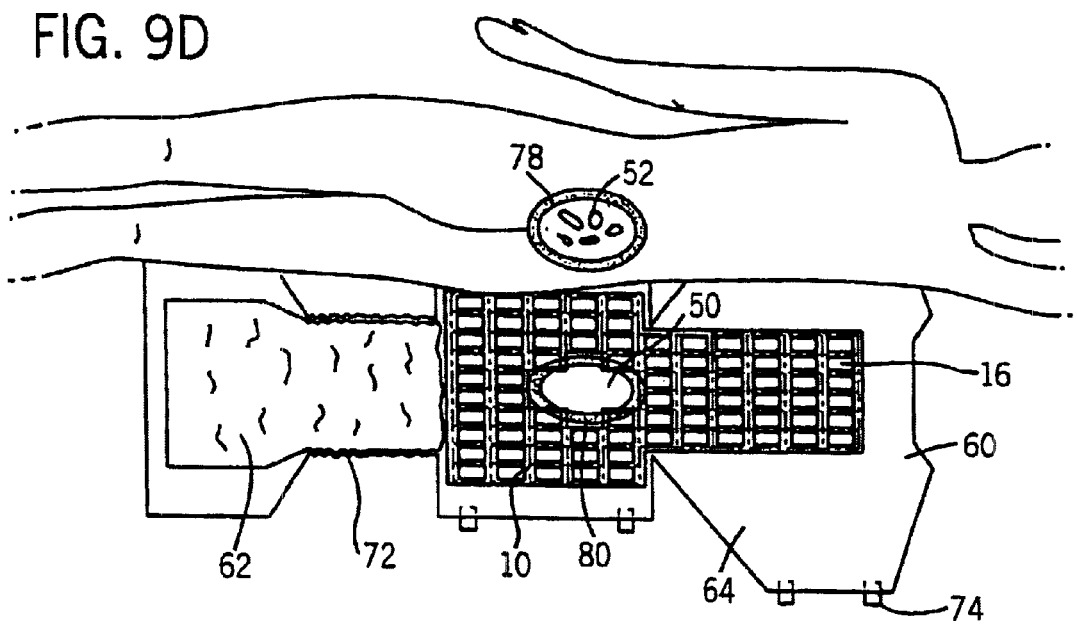

As shown in FIG. 9C, once the suspension device 10 of the disposable garment 60 is positioned against the user, the dye 78 outlining the target area 52 is transposed to the inner surface of the suspension system 10 of the disposable garment 60. The disposable garment 60 is then removed from contact with the user's body and contains a portion of the dye 78 used to mark the outline of the target area 52. As shown in FIG. 9D, specific bubbles 16 are then selectably removed from the suspension system 10 in order to create the custom fit opening 50 within the suspension device 10 which substantially matches the outline of the target area 52. Once the bubbles 16 have been removed from the suspension system 10, a double sided tape 80 can then be applied to the inner surface of the suspension system 10 in order to strengthen the border of the opening 50 created in the suspension system 10. The double sided tape 80 also provides additional contact with the user in order to further secure and prevent the repositioning of the disposable garment 60 on the user's body. The tape 80 is a conventional non-toxic double sided tape. Alternative, fasteners can also be used such as, for example, single-sided tape, or adhesives.

Figure 9E:
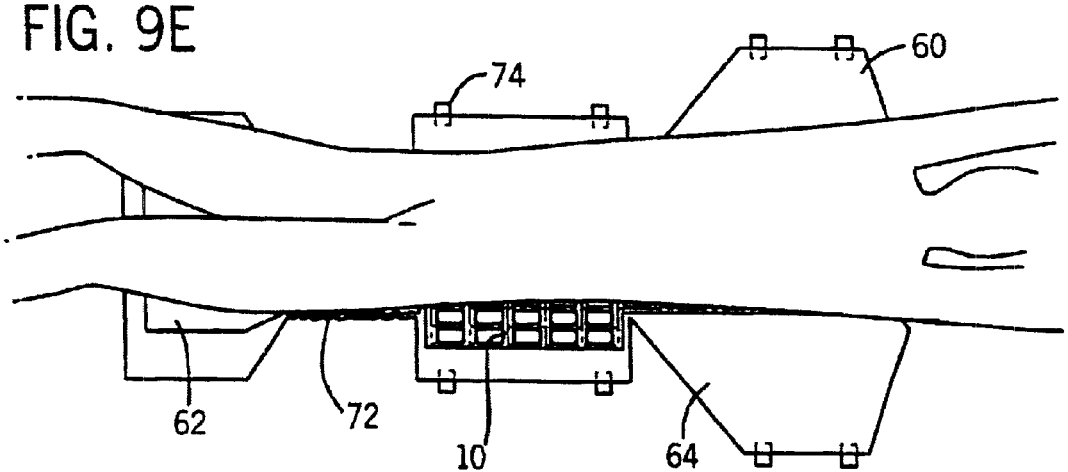
Figure 9F:
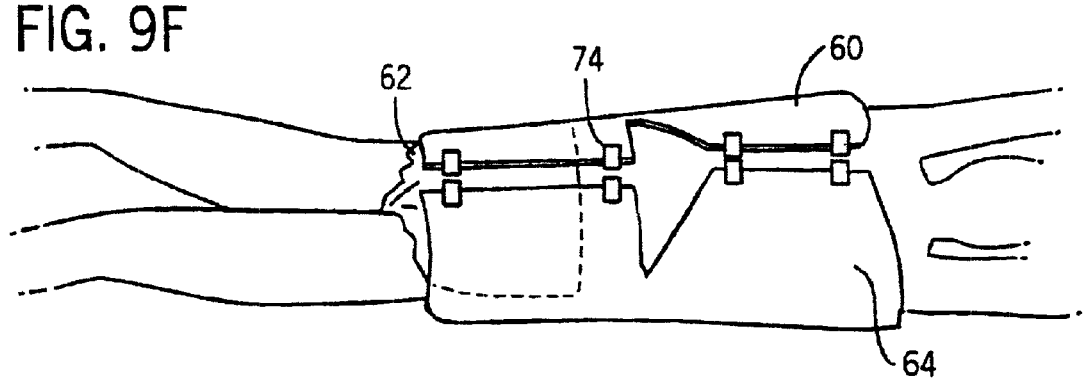

As shown in FIG. 9E, the user is rolled and repositioned onto his or her back. As shown in FIG. 9F, the absorbent portion 62 of the disposable garment 60 is then extended through the user's legs and is placed up against the abdomen of the user's body. The panels 64 are then secured around the user's body and releasably connected to one another through the straps 74. In alternative embodiments, this method can be applied to disposable garments configured to fit on other parts of the user's body for example a leg, an arm a hip, etc.

Figure 10:
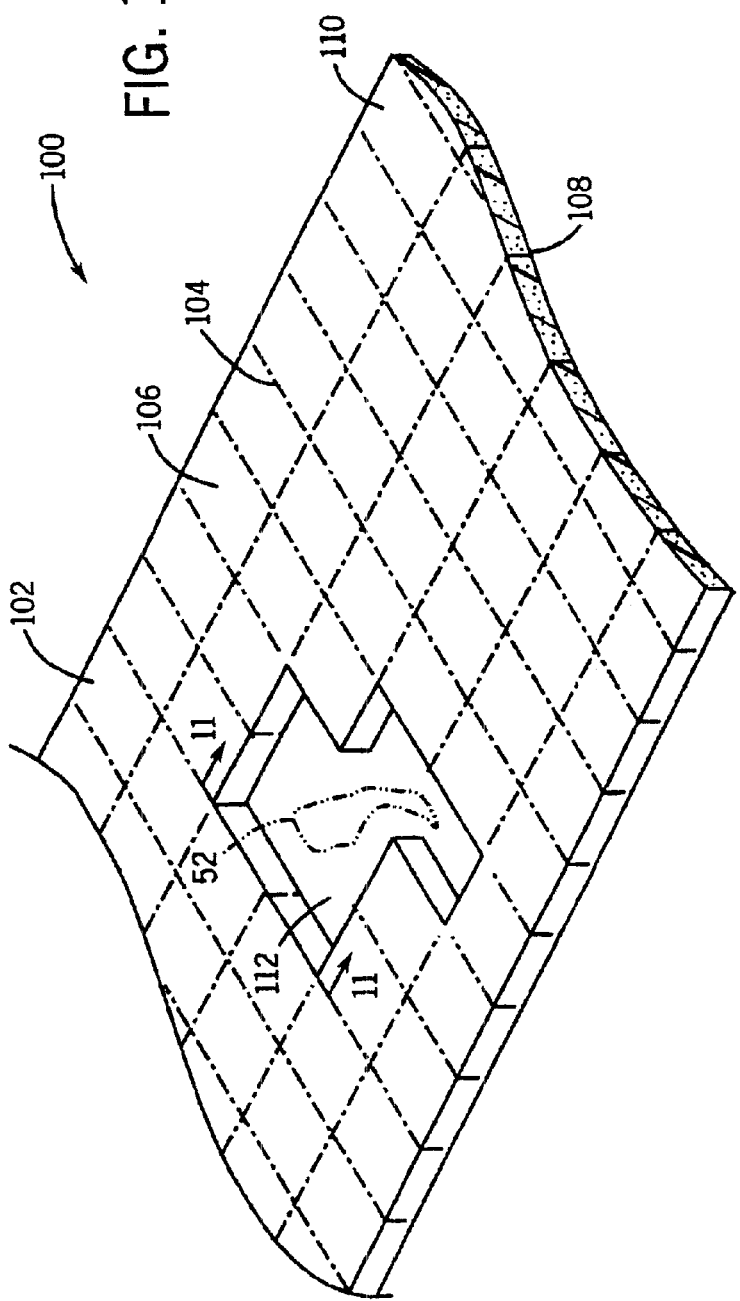
FIG. 10 is a top perspective view of a section of a wound care suspension system in accordance with another alternative preferred embodiment of the present invention.
Figure 11:
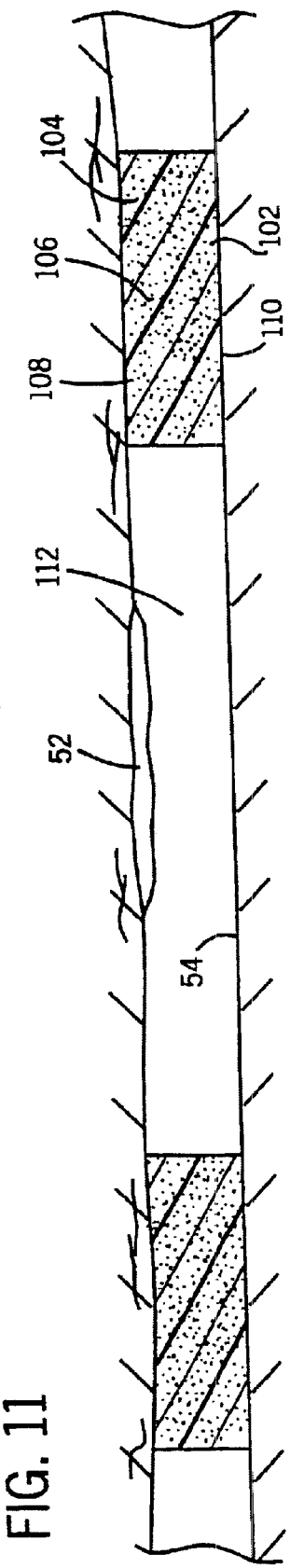
FIG. 11 is a sectional view of the wound care and suspension system taken substantially along line 11—11 of FIG. 10.

In an alternative preferred embodiment as shown in FIGS. 10 and 11, the suspension system 100 includes a single sheet 102 of flexible, cushionable material. The sheet 102 includes a plurality of grooves 104 arranged in a criss-cross pattern to define a plurality of individual stanchions 106. The grooves 104 are defined within the sheet to extend from an inner surface 108 of the sheet 102 toward, but not completely through the sheet 102, to an outer surface 110 of the sheet 102. The grooves 104 can be formed into the sheet by an electric knife or other forming tool. The grooves 104 enable a user to easily and selectably "pinch and pull" out one or more stanchions 106 from the sheet 102 in order to define an opening 112 within the sheet 102 that is custom fit to the target area 52 on the user's body. The cushionable material of the sheet 102 comfortably and evenly supports the portion of the user's body in contact with the sheet 102 above the resting surface 54 and comfortably suspends the target area 52 of the user's body above the resting surface 54. The suspension material is preferably made of a non-latex, non-allergenic, medical grade polyurethane foam and alternatively can be made of other materials such as, for example, other conventional foams or sponge material. The system 100 is an inexpensive, versatile and flexible system for the care and prevention of wounds. In a preferred embodiment, the stanchions 106 are approximately 0.5 square inch rods having a thickness of approximately 1.0 inches. In an alternative embodiment, the sheet 100 can include a backing (not shown) and a soft patient contact layer (not shown).

In another preferred embodiment shown in FIG. 12, the suspension system 200 is a flexible sheet 202 comprised of two separate layers of material connected along a plurality of borders 204 to form a plurality of bubbles 206. Each border 204 connects at least two bubbles 206 together and includes perforations 208 to facilitate the removal of one or more bubbles 206 from the sheet 202 in order to define a custom fit opening 210. The perforations 208 also enable air to pass through the sheet 202 to ventilate the portion of the user's body in contact with the suspension system 200.

In another preferred embodiment shown in FIG. 13, the system 300 is a sheet of gas-filled bubbles 302 and includes a pricking device 304. The pricking device 304 is a hand-held instrument configured to pop one or more of the bubbles 302 (forming a deflated bubble 308) within the system 300 in order to create a space 306 between the target area 52 and the portion of the system 300 with the collapsed bubbles. The pricking device 304 can be removably attached to the system 300 packaged along with the system 300, or sold separately from the system 300. The pricking device 304 enables a user to selectably burst or deflate one or more gas-filled bubbles in order to custom define a space between the target area 52 of the user's body and the portion of the system 300 with the collapsed bubbles.

While preferred embodiments of the present invention have been described and illustrated, numerous departures therefrom can be contemplated by persons skilled in the art, for example, the suspension system, in lieu of bubbles, can be comprised of a plurality of hollow tubes in a variety of different shapes or sizes. Therefore, the present invention is not limited to the foregoing description but only by the scope and spirit of the appended claims.

What is claimed is:

1. A support device for the care and prevention of wounds on a target area of the body of a user, comprising:
    means for reducing pressure friction and shear that can irritate or cause ulcers resulting from prolonged contact between the target area of the body of the user and a chafing surface,
    said means for reducing pressure, friction and shear having an array of removable cells forming a flexible sheet for supporting an area of the body of the user, each cell removably coupled to at least one other cell, at least one of the cells being a cell that is selectably removable from the array in order to define a space in the sheet which approximates the size of the target area on the body of the user, and
    said means for reducing pressure, friction and shear encloses the target area, whereby, the support device forms a peripheral support enclosure about a target area.

2. The device of claim 1 wherein each cell has a border and is removably connected to at least one other cell along a portion of the border.

3. The device of claim 1 wherein the cells are suspension devices.

4. The device of claim 1 wherein the removable cells have opposing first and second surfaces and the first surface of each cell is configured for contacting the user.

5. The device of claim 4 further comprising a backing coupled to the second surface of the removable cells.

6. The device of claim 4, wherein the space within the sheet is defined by and extends from the first surface through the sheet to the second surface.

7. The device of claim 5, wherein the backing includes perforations positioned substantially along a border of each cell.

8. The device of claim 7, wherein the second surface comprises one of a hook material and a loop material and the backing comprises the other of the hook material and the loop material.

9. The device of claim 5, wherein each cell is removably connected to the backing.

10. The device of claim 5, wherein the backing is attached to the sheet such that when at least one cell is removed from the sheet, a portion of the backing in contact with the cell is removed from the backing creating an opening in the backing which next to the space within the sheet.

11. The device of claim 1, wherein the cells are gas-filled bubbles.

12. The device of claim 11, further comprising a pricking device for selectably deflating at least one of the bubbles.

13. The device of claim 1 wherein at least a portion of each cell is made of a breathable material.

14. The device of claim 1, further comprising a dye configured for marking an approximate outline of the target area onto the first surface of the array of removable cells.

15. The device of claim 1, wherein the removable cells are stanchions made of a cushionable material.

16. The device of claim 1, wherein the array of cells is configured to support the target area of the user's body without contacting the target area.

17. A support device for the care and prevention of wounds on a target area of the body of a user, comprising:
    means for reducing pressure, friction and shear that can irritate or cause ulcers resulting from prolonged contact between the target area of the body of the user and a chafing surface,
    said means for reducing pressure, friction and shear having an array of removable cells forming a flexible sheet for supporting an area of the body of the user adjacent the target area, each cell removably coupled to at least one other cell, the cells being selectably removable from the array in order to define a space in the sheet which approximates the size of the target area on the body of the user,
    said space having one of a flexible cover and of being free of a cover.

18. The support device of claim 17, wherein each cell has a border and is removably connected to the at least one other cell along a portion of the border, said portion of the border having means for separating to allow at least one selected cell to be separated from the at least one other cell by hand and removed from the sheet by the user independent of a tool.

19. A support device for the care and prevention of wounds on a target area of the body of a user, comprising:
    means for supporting the target area above the bed in which the user is confined to reduce pressure, friction and shear that can irritate or cause ulcers resulting from prolonged contact between the target area of the body of the user and a chafing surface,
    said means for supporting having an array of removable cells forming a flexible sheet for supporting an area of the body of the user proximate the target area, each cell removably coupled to at least one other cell, each cell has a border and is removably connected to the at least one other cell along a portion of the border, said portion of the border having means for separating to allow at least one selected cell to be separated from the at least one other cell by hand and removed from the sheet by the user independent of a tool in order to define a space in the sheet which approximates the size of the target area,
    said space having one of a flexible cover and of being free of a cover.

20. The support device of claim 19, further comprising means for ventilating the area of the body of the user proximate the target area.

21. A support device for the care and prevention of wounds on a target area of the body of a user confined to a bed, comprising:
    means for reducing pressure, friction and shear that can irritate or cause ulcers resulting from prolonged contact between the target area of the body of the user and the bed or a bed sheet of the bed in which the user is confined, said means for reducing pressure, friction and shear having an array of removable cells forming a flexible sheet for supporting an area of the body of the user, each cell removably coupled to at least two other cells, at least one of the cells being an interior cell that is selectably removable from the array in order to define an interior space within the sheet which approximates the size of the target area on the body of the user, and said means for reducing pressure, friction and shear encloses the target area, whereby, the support device forms a continuous peripheral support enclosure about a target area.

22. A support device for the care and prevention of wounds on a target area of the body of a user, comprising: means for reducing pressure, friction and shear that can irritate or cause ulcers resulting from prolonged contact between the target area of the body of the user and a chafing surface, said means for reducing pressure, friction and shear having an array of removable cells forming a flexible sheet for supporting an area of the body of the user, each cell removably coupled to at least one other cell, at least one of the cells being an interior cell that is selectably removable from the array in order to define an interior space within the sheet which approximates the size of the target area on the body of the user, and said means for reducing pressure, friction and shear encloses the target area, whereby, the support device forms a continuous peripheral support enclosure about a target area.

* * * * *